US006255057B1

(12) United States Patent
Gordon et al.

(10) Patent No.: US 6,255,057 B1
(45) Date of Patent: *Jul. 3, 2001

(54) DETECTION OF CELLULAR EXPOSURE TO ETHANOL

(75) Inventors: Adrienne Sue Gordon, Kensington; Ivan Diamond, Berkeley; Doug Paul Dohrman, San Francisco, all of CA (US)

(73) Assignee: Ernest Gallo Clinic and Research Center, Emeryville, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/686,796

(22) Filed: Jul. 26, 1996

(51) Int. Cl.[7] .................. G01N 33/53; G01N 33/535; G01N 33/573; G01N 33/98
(52) U.S. Cl. .................. 435/7.21; 435/7.4; 435/7.9; 435/19; 436/503
(58) Field of Search .................. 435/7.21, 7.4, 435/7.9, 19; 436/503

(56) References Cited

U.S. PATENT DOCUMENTS 5,069,895  12/1991  Diamond et al. .................. 424/10

OTHER PUBLICATIONS

Gayer, G.G., et al., 1991, "Ethanol Increases Tyrosine Hydroxylase Gene Expression in N1E–115 Neuroblastoma Cells," *J. Biol. Chem.* 266:22279–22284.

Gerstin, E., et al., 1996, "Protein Kinase C Isozymes Required for Up–regulation of L–type Calcium Channels by Ethanol," *Supp. Alcholism Clinical and Experimental Research* 20:102A.

Gordon et al., 1986, "Ethanol Regulation of Adenosine Receptor–stimulated cAMP Levels in a Clonal Neural Cell Line: An in vitro Model of Cellular Tolerance to Ethanol," *Proc. Natl. Acad. Sci USA* 83:2105.

Heberlein, U., et al., 1993, "Star is Required for Neuronal Differentiation in the Drosophila Retina and Displays Dosage–Sensitive Interactions with Ras1," *Dev. Biol.* 160:51–63.

Hundle, B., et al., 1995, "An ε–PKC–derived Peptide Fragment Prevents Enhancement of NGF–induced Neurite Outgrowth by Phorbol Esters and Ethanol," *9th International Conference on Second Messengers & Phosproteins* 151.

Hundle, B., et al., 1995, "Overexpression of ε–Protein Kinase C Enhances Nerve Growth Factor–induced Phosphorylation of Mitogen–activated Protein Kinases and Neurite Outgrowth," *J. Biol. Chem.* 270:30134–30140.

Messing, et al., 1990, "Protein Kinase C Participates in Up–Regulation of Dihydropyridine–Sensitive Calcium Channels by Ethanol," *J. of Neurochem.* 55:1383–1389.

Messing, et al., 1991, "Chronic Ethanol Exposure Increases Levels of Protein Kinase C δ and ε and Protein Kinase C–mediated Phosphorylation in Cultured Neural Cells," *J. Biol. Chem.* 266:23428–23432.

Miles, M.F., et al., 1991, "Mechanisms of Neuronal Adaptation to Ethanol," *J. Biol. Chem.* 266:2409–2414.

Miles, M.F., et al., 1993, "Phosducin–like Protein: An Ethanol–responsive Potential Modulator of Guanine Nucleotide–binding Protein Function," *Proc. Natl. Acad. Sci. USA* 90:10831–10835.

Mochly–Rosen, D., et al., 1988, "Chronic Ethanol Causes Heterologous Desensitization of Receptors by Reducing $\alpha_s$ Messenger RNA," *Nature* 333:848–850.

Mochly–Rosen, 1995, "Localization of Protein Kinases by Anchoring Proteins: A Theme in Signal Transduction," *Science* 268:247.

Nagy, L.E., et al., 1989, "Adenosine is Required for Ethanol–induced Heterologous Desensitization," *Mol. Pharm.* 36:744–748.

Nagy, L.E., et al., 1991, "cAMP–dependent Protein Kinase Regulates Inhibition of Adenosine Transport by Ethanol," *Mol. Phar.* 40:812–817.

Nagy, L.E., et al., 1988, "Cultured Lymphocytes from Alcoholic Subjects have Altered cAMP Signal Transduction," *Proc. Natl. Acad. Sci. USA* 85:6973–6976.

(List continued on next page.)

Primary Examiner—Gary L. Kunz
Assistant Examiner—Robert C. Hayes
(74) Attorney, Agent, or Firm—Cooley Godward LLP

(57) ABSTRACT

The present invention relates to determinable effects of ethanol exposure on the cellular localization and abundance of specific proteins, referred to herein as ethanol indicative proteins. More specifically, the present invention is based, in part, on the discovery that the catalytic Cα subunit of cAMP dependent protein kinase (PKA), which is normally localized in the Golgi apparatus area, appears to translocate to the nucleus upon exposure of a cell to ethanol. The present invention is further based on the observation that the δ-subunit of PKC translocates from the Golgi area to the perinucleus and the nucleus in response to ethanol exposure, while the ε-subunit of PKC migrates from the perinucleus into the cytoplasm. The present invention further relates to the discovery that the detectable amount of the regulatory subunit RI of PKA decreases, while the detectable amount of αPKC, δPKC and εPKC increases upon exposure of a cell to ethanol. These discoveries provide the basis for assays that may be used to detect the exposure of cells to ethanol and assays that may be used for the screening of drugs or the development of treatments to modulate the effects of ethanol consumption. The invention further relates to kits for detecting the exposure of cells to ethanol. Kits of the invention may include antibodies, which preferably are labeled, capable of specifically binding to Cα or RI of the cAMP-dependent protein kinase, or, capable of specifically binding to αPKC, δPKC or εPKC.

25 Claims, 9 Drawing Sheets

OTHER PUBLICATIONS

Roivainen, R., and Messing, R.O., 1993, "The Phorbol Derivatives Thymeleatoxin and 12–deoxyphorbol–13–O–phenylacetate–10–acetate Cause Translocation and Down–Regulation of Multiple Protein Kinase C Isozymes," *FEBS* 319:31–34.

Roivainen, et al., 1993, "Protein Kinase C Isozymes that Mediate Enhancement of Neurite Outgrowth by Ethanol and Phorbol Esters in PC12 Cells," *Brain Research* 624:85–93.

Roivainen, R., et al., 1995, "Ethanol Enhances Growth Factor Activation of Mitogen–activated Protein Kinases by a Protein Kinase C–dependent Mechanism," *Proc. Natl. Acad. Sci. USA* 92:1891–1895.

Roivainen, B., et al., 1994, "Protein Kinase C and Adaptation to Ethanol," *Toward a Molecular Basis of Alcohol Use and Abuse* 29–38.

Wilke, N., et al., 1994, "Effects of Alcohol on Gene Expression in Neural Cells," *Toward a Molecular basis of Alcohol Use and Abuse* 49–59.

CONTROL

ETHANOL

PGE$_1$

FORSKOLIN

PKC δ

CONTROL

EtOH 200 mM

PMA

PKC δ

CONTROL

EtOH
25 mM

Pre.

PKC ε

CONTROL

EtOH
200 mM

PMA

PKC ε

CONTROL

EtOH
25 mM

Pre.

DETECTION OF CELLULAR EXPOSURE TO ETHANOL

The present invention was made with Government support under Grants R01 AA10030 and R01 AA10039 awarded by the National Institute of Health. The Government has certain rights in the invention.

FIELD OF THE INVENTION

The present invention is in the field of biological assays for the detection of ethanol exposure in mammals and for the evaluation of drugs that modify the cellular effects of ethanol consumption.

BACKGROUND OF THE INVENTION

The abuse of ethanol remains a major public health problem in the U.S. and throughout the world. It is of interest to provide methods for the detection of ethanol exposure in individuals so as to monitor compliance with abuse treatment regimens. It is also of interest to provide assays useful for the evaluation of drugs that may be used to treat one or more of the adverse effects of chronic ethanol overconsumption. In order to provide such methods and assays, it is necessary to gain detailed understanding of the biochemical effects of ethanol exposure at a cellular level. Recent evidence suggests that ethanol modifies the function of certain proteins and signal transduction pathways, thereby producing changes in second messenger concentrations, protein kinases, and gene expression. This observation does not provide a specific test which enables the effects of ethanol to be readily determined. Recently, it has been shown that the specificity of protein kinases appears to correlate with their localization within the cell. Mochly-Rosen, 1995, *Science* 268:247.

Chronic alcoholism causes functional and pathologic changes in many organs, particularly the brain, but the molecular mechanisms which account for these effects are not well understood. It would be desirable to provide methods for monitoring the effect of chronic ethanol exposure on mammalian cells, and further desirable to provide methods for determining if an individual has been actively consuming ethanol for extended periods of time.

The present invention relates to an assay for detecting the effects of ethanol, particularly the chronic exposure of ethanol, on animal cells, particularly human or other mammalian cells. This assay can be used both in a diagnostic test to determine ethanol consumption in an individual, or in screening for drugs or treatments which moderate, inhibit, reverse or enhance the effects of ethanol consumption.

SUMMARY OF THE INVENTION

The present invention relates, in part, to the discovery that exposure to ethanol alters dramatically the subcellular localization of the catalytic $C\alpha$ subunit of the cAMP dependent protein kinase (PKA) and the $\delta$- and $\epsilon$-subunits of protein kinase C (PKC). For example, the catalytic $C\alpha$ subunit of PKA, which is normally localized to the Golgi apparatus area, appears to translocate to the nucleus upon exposure of a cell to ethanol. Ethanol also has been shown to cause translocation of PKC activity from cytosolic to membrane fraction in astroglial cells and human lymphocytes and epidermal keratinocytes. The present invention further relates to the discovery that the detectable amount of the regulatory subunit RI of PKA decreases, and the amounts of the $\alpha$-, $\delta$- and $\epsilon$-subunits of PKC increase in certain cell types, including but not limited to, NG108-15 cells ($\alpha$-, $\delta$-, and $\epsilon$-subunit) or PC12 cells ($\delta$- and $\epsilon$-subunit), upon the exposure to ethanol. These discoveries provide the basis for assays that may be used to detect the exposure of cells to ethanol and further for assays that may be used for the screening of drugs or treatment to modulate the effects of ethanol consumption.

One aspect of the invention is to provide assays that provide an indication of the exposure of a cell or an individual to ethanol by identifying at least one cell component, e.g., a protein, that has a cellular localization (distribution) that varies in correlation with the exposure of the cell to ethanol, and determining the distribution of that cell component within a cell of a sample to be tested. In one preferred embodiment, the cell component comprises a subunit of the cAMP dependent protein kinase, PKA, the $C\alpha$ subunit being particularly preferred. In another preferred embodiment, the cellular component comprises an isozyme protein kinase C, PKC, wherein the $\delta$ or the $\epsilon$ isozyme of protein kinase C is particularly preferred.

Another aspect of the invention is to provide assays that provide an indication of exposure of a cell or an individual to ethanol by measuring the amount of protein that varies in amount in a relationship with the exposure of the cell to ethanol. In one preferred embodiment, the decrease of the detectable amount of the regulatory subunit RI of PKA in response to ethanol exposure is determined. In another preferred embodiment, the increase of the detectable amounts of $\alpha$PKC, $\delta$PKC, or $\epsilon$PKC in response to ethanol exposure is measured.

Another aspect of the invention is to provide assays for screening therapeutic compounds that modulate the effects of ethanol on a cell. These screening assays measure the effects of a compound of interest to interfere with one or more of the cellular effects of ethanol described herein, i.e., changes in the localization of $C\alpha$, $\delta$PKC, or $\epsilon$PKC, decreases in the amount of RI, increases in the amount of $\alpha$PKC, $\delta$PKC, or $\epsilon$PKC, changes in the set of proteins phosphorylated by or expressed in response to $C\alpha$, $\delta$PKC and $\epsilon$PKC. For example, $C\alpha$ may induce phosphorylation of CREB and thereby its activation, resulting in the induction of CRE-regulated gene expression. Another aspect of the invention is to provide kits for detecting the exposure of cells to ethanol. Kits of the invention may include labeled antibodies capable of specifically binding to $C\alpha$ or RI of PKA or to the $c\alpha$-, $\delta$- and $\epsilon$-subunits of PKC, respectively.

DEFINITIONS

Figure 1A:
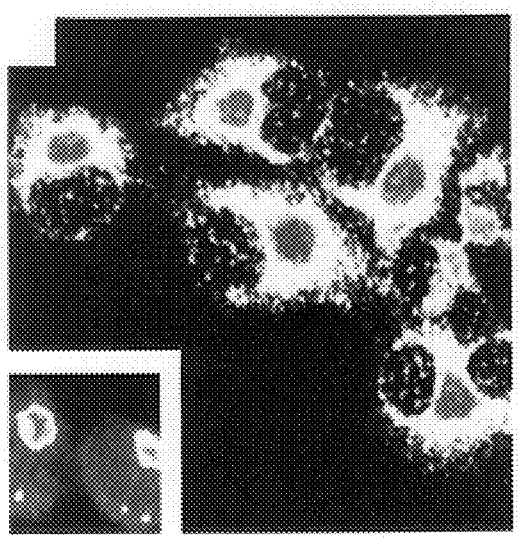
FIGS. 1A–D shows micrographs indicating the location of the PKA catalytic subunit staining in NG108-15 cells after a forty eight (48) hour exposure to 200 mM ethanol. The images in panels (A) and (B) were made with a confocal microscope, whereas those in panels (C) and (D) were made with a light microscope with a fluorescein filter. The inserts shown in panel (A) and panel (B) are also obtained by a light microscope. Panel (A) represents control cells wherein the majority of staining exists in the perinuclear golgi area. Panel (B) represents test cells exposed to ethanol. As can be seen from the image, the staining is primarily within the nuclear region. Panel (C) represents an image showing the reversibility of the distribution of staining upon withdrawal of ethanol from the cells. Panel (D) represents a test for the specificity of the stain, when anti-$C\alpha$ antibody was preabsorbed by purified $C\alpha$ prior to labelling of the cell. As can be seen, no staining resulted, indicating that the stain is specific for $C\alpha$.
Figure 1B:
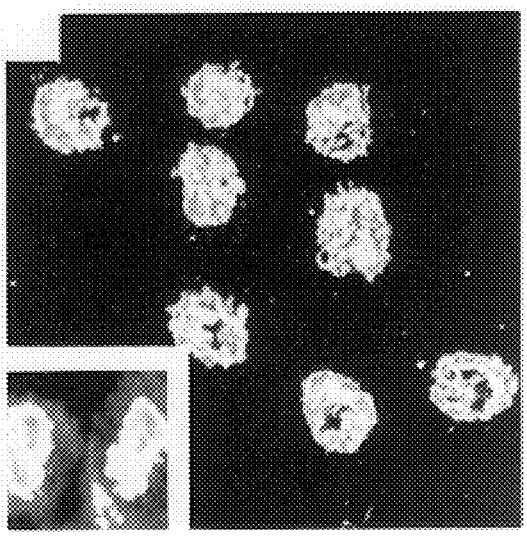
Figure 1C:
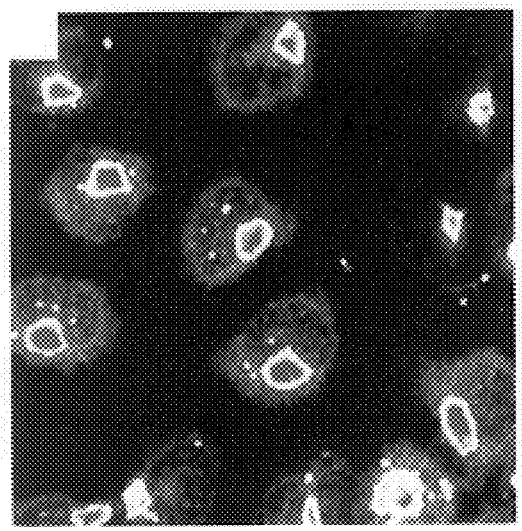
Figure 1D:
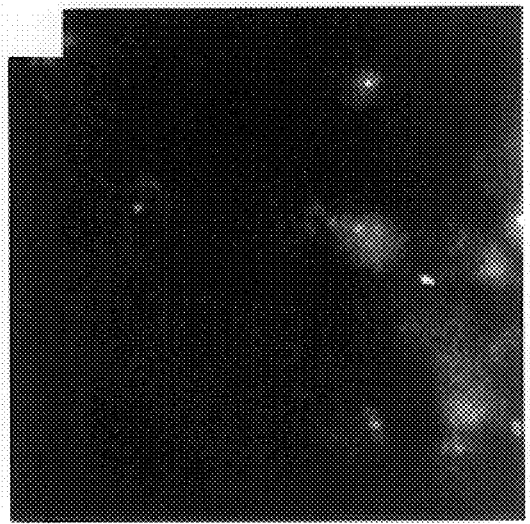

As used herein, the following term(s), whether used in the singular or plural, will have the meanings indicated:

Ethanol Indicative Protein. As used herein, the term ethanol indicative protein refers to a gene product whose cellular localization or detectable amount changes in response to exposure to ethanol.

DETAILED DESCRIPTION OF THE INVENTION

The subject invention relates to discoveries concerning the effects of ethanol on the cellular localization and abundance of specific proteins as a consequence of exposure of cells to ethanol. Specifically, the invention relates to the discovery that the exposure of cells to ethanol induces translocation of the Cα catalytic subunit of cAMP-dependant protein kinase (PKA) from the Golgi region to the nucleus. The invention relates further to the discovery that exposure of cells to ethanol induces translocation of the δ-subunit of PKC from the Golgi region to the perinucleus and the nucleus, while inducing translocation of the ε-subunit of PKC from the perinucleus to the cytoplasm. Additionally, the invention relates to the discovery that the detectable amount of type I (RI) regulatory subunit of PKA found in cells decreases in response to ethanol exposure, while the detectable amounts of αPKC, δPKC, and εPKC increase in response to short term as well as long term exposure to ethanol. The cellular changes in response to ethanol exposure have numerous consequences beyond the effects of ethanol on cellular localization of Cα and δPKC and εPKC. For example, the dissociation of the catalytic subunit Cα from the regulatory subunit frees the Cα subunit to phosphorylate proteins. Furthermore, by translocating to the nucleus, the Cα subunit of PKA may phosphorylate a different set of proteins than those available in the Golgi apparatus or elsewhere in the cytoplasm. Moreover, the translocation of the Cα subunit may also alter the extent of phosphorylation of different proteins phosphorylated by Cα, such as CREB, as well as it may alter the CRE-regulated gene expression. The Cα-mediated changes in protein phosphorylation may also have detectable effects on gene expression; such PKA effects may also be used to monitor ethanol exposure. Similar effects of δPKC and εPKC translocation may be determined. Generally, proteins whose cellular localization or detectable amount are altered by ethanol exposure are referred to herein as ethanol indicative proteins.

In one aspect, the present invention provides a method for determining ethanol exposure of a sample containing at least one cell, comprising identifying a protein having a location that is substantially affected by exposure to ethanol, and determining the distribution of the protein within the cell, thereby producing an indication of the exposure of the cell to ethanol. In one specific embodiment, the protein is the Cα catalytic subunit of cAMP-dependant protein kinase (PKA). In another specific embodiment, the protein is the δ- or ε-isozyme of the protein kinase C (PKC). The step of identifying preferably comprises staining the cell with a staining complex having specific binding affinity for the protein. The step of determining the location of the protein preferably includes imaging or observing the cell using conventional imaging techniques, e.g., a microscope. Preferably, the sample contains a plurality of cells, and the determination is carried out for several of the plurality of cells. Preferably, the cells analyzed are derived from blood samples, e.g., lymphocytes, granulocytes, etc. Nuclear accumulation of the ethanol indicative protein, e.g., the Cα of PKA, δPKC or εPKC may also be assessed by observing Cα-, δPKC-, or εPKC-induced cellular events. For example, it may be possible to observe the chronic activation of CREB transcription factor and other nuclear substrates in response to Cα-activation.

The methods of the invention may be employed to monitor withdrawal of ethanol from a subject. Specifically, after a chronic alcoholic withdraws from alcohol, it is expected that Cα and δPKC will leave the nucleus or nucleus and perinucleus, respectively, and return to the Golgi, while εPKC will return from the cytoplasm to the perinuclear region. Thus, the techniques described may be used to monitor the withdrawal from ethanol over a relatively short period of time.

The invention provides methods for determining exposure of cells to ethanol comprising the steps of applying a stain using specific affinity for the ethanol indicative protein, e.g., the Cα-subunit of PKA, or the δ- or ε-PKC isozyme to the sample so as to identify the region or regions of the cell that contain Cα, δPKC, or εPKC, respectively. After the regions of the cell containing PKA or PKC have been identified, the cell or cells are classified as to the distribution of the stain within the cells, wherein localization of Cα stain in the cell nucleus, δPKC in the perinucleus and the nucleus, and εPKC stain in the cytoplasm is indicative of prior exposure of the cell to ethanol. Cells that contain significant, i.e., greater than control cells, detectable amounts of stain for Cα of PKA in the nucleus, the δ-subunit of PKC in the perinucleus and nucleus, or εPKC in the cytoplasm, respectively, are indicative as being exposed to ethanol.

Advantageously, the determination of cellular localization of the ethanol indicative protein, e.g., Cα, δPKC or εPKC, comprises identifying first and second regions within each cell, and classifying cells as a first type if the protein is predominately present in a first region, and as a second type if the protein is predominately present in the second region. The number of cells of the first type may be compared to the number of cells of the second type for a determined number of cells within a sample. A number dependent on the proportion of cells of the first and second types, usually the ratio or percentage, may be correlated with a control derived from reference data to obtain a qualitative determination of whether exposure to ethanol of the sample has exceeded a certain threshold, or to obtain a semi-quantitative determination of the exposure to ethanol of the sample. In the case of Cα, the first region will preferably be the nucleus of the cell, and the second region will preferably be the perinuclear Golgi apparatus. In the case of δPKC, the first region will preferably be the perinucleus and the nucleus of the cell, and the second region will preferably be the perinuclear Golgi apparatus. In the case of εPKC, the first region will preferably be the cytoplasm of the cell, and the second region will preferably be the perinucleus and the nucleus of the cell. The control will depend on the type of cells being examined and will usually be about 25–35%, i.e. if more than 25–35% of the cells display localization in the first region, the sample will be positive.

The classification step includes the step of identifying the cellular location of the stain and hence the location of the ethanol indicative protein, e.g., the Cα-subunit of PKA, δPKC or εPKC or any other proteins with comparable localization behavior. The precise means of identifying the cellular location of the ethanol-indicative protein, e.g., Cα, δPKC or εPKC will vary with label used in the stain. Generally, a variety of methods may be used for each type of label selected. For example, a radioisotope label may be detected through film (autoradiography), Charge Coupled Devices (CCDs) and the like.

When analyzing the results of the subject assays in which a sample containing a plurality of cells is stained with ethanol indicative protein, e.g., Cα, δPKC or εPKC-, specific stain, the percentage of cells that show altered location of the ethanol indicative protein must be considered. Not every ethanol exposed cell in a sample will show altered location of the ethanol indicative protein. However, significantly more cells with altered location of the ethanol indicative protein will be found in multiple cell containing samples that have been exposed to ethanol as opposed to control samples. Furthermore, the percentage of cells showing altered location of the ethanol indicative protein, i.e., translocation to the nucleus in the case of Cα, translocation to the perinucleus and the nucleus in the case of δPKC, or translocation to the cytoplasm in the case of εPKC, is expected to increase with increasing duration of exposure to ethanol and with increasing amount of ethanol to which the cells are exposed. Statistical analysis may be used to develop quantitative correlations between the percentage of cells in a sample sharing altered location of the ethanol indicative protein and the amount of exposure. Other factors to consider when making such correlations include the age and condition of the source of the cell sample, the particular cell type being analyzed, and the like. The sample may be taken from a live subject, for example a human whose ethanol consumption is to be measured. Alternatively, cells cultured in vitro may be used in those embodiments of the invention that are directed to the monitoring of ethanol in subjects, e.g., screening for therapeutic agents. Where the sample is taken from a live subject, the sample is preferably a blood-sample, containing nucleated cells, such as granulocytes and lymphocytes.

The ethanol consumption of a subject, particularly a human, could in principle be determined by assaying the cells obtained from the subject. Cells for analysis in the subject assays for ethanol exposure may come from a variety of locations within the body. Cell containing samples may be obtained from organs or non-organ tissue. Preferably, cell containing samples are obtained from easily removed tissues such as blood and skin. Because of the transient and reversible effects of ethanol on ethanol indicative proteins, e.g., Cα, δPKC, εPKC, it is important that samples be analyzed with the assays of the invention as soon as possible after the sample is removed from a subject for analysis. Localization of ethanol indicative proteins such as the Cα subunit of PKA, δPKC, or εPKC in granulocytes and/or lymphocytes can be investigated. Both of these cell types can be conveniently obtained from blood samples. To determine the effect of ethanol consumption in a particular individual, a comparison can be made between the proportion of cells having, e.g., predominately nuclear localization of Cα, perinuclear and nuclear localization of δPKC, or cytoplasmic localization of εPKC, to that obtained from a reference sample. To monitor progress of the individual over time, a number of samples can be taken, and variations in the localization of staining can be monitored. The technique can be used to determine the effects of a treatment on a live subject, by monitoring changes in the subject when provided with the treatment.

In another aspect, the present invention provides a method of measuring the exposure to ethanol of a sample containing at least one cell, the method comprising measuring, either quantitatively or qualitatively, the amount of a protein or polypeptide, which amount is dependent on exposure of the cell to ethanol, and determining the amount of the protein in the cell. In one preferred embodiment, the polypeptide may be the type I regulatory subunit (RI) of PKA where a reduction, for example a 20% to 50% reduction compared to control cells not exposed to ethanol, is indicative of ethanol exposure. Alternatively, the detectable amount of the protein heat stable protein kinase inhibitor (PKI) may be measured and correlated with ethanol exposure. In another preferred embodiment, the increase of the detectable amount of the α-, δ-, or the ε-subunit of PKC may be determined and correlated with ethanol exposure. The determination may be carried out by any of a variety of measurement methods well known to persons of ordinary skill in the art of molecular biology, such methods include ELISA, radioimmunoassay, western blot analysis, and the like.

The methods described herein may be used in screening drugs for their efficacy in moderating the effects of ethanol by measuring the effects of ethanol on a sample treated with the drug and exposed to ethanol, and comparing the results with results obtained from a control sample exposed to ethanol but not treated with the drug. The methods may also be used for providing an indication of the effects of ethanol consumption in a subject individual by comparing the results obtained with reference results, for example results obtained from a control subject, either in vitro or in vivo, or to other measurements taken from the same subject over a period of time to determine progress of alcoholism or of treatments. Numerous other applications will become apparent to those skilled in the art.

Using known immunocytochemistry techniques, a stain specific for the ethanol-indicative protein, e.g. the Cα catalytic subunit of PKA, αPKC, δPKC or εPKC is prepared.

Stains specific for RI and other proteins having cellular locations or quantities that may be correlated with ethanol exposure may be similarly prepared and used for the quantitative detection of, i.e., RI. The stain comprises a specific binding substance which binds specifically to the targeted ethanol indicative protein, e.g., the Cα subunit of PKA, αPKC, δPKC, εPKC, RI, for example an antibody and a labelling moiety. Suitable antibodies may be prepared using conventional antibody production techniques. The antibodies may be monoclonal or polyclonal. The antibodies may also be obtained from genetically engineered hosts or from conventional sources. Antibodies may be prepared in response to the ethanol indicative protein, e.g., Cα, cαPKC, δPKC, εPKC, or RI, or immunologically cross-reactive fragments thereof. Techniques for antibody production are well known to the person of ordinary skill in the art, examples of such techniques can be found in Harlow and Lane, *Antibodies: A Laboratory Manual*, Cold Spring Harbor Laboratory Press, Cold Spring Harbor (1988), Birch and Lennox, *Monoclonal Antibodies: Principles and Applications*, Wiley-Liss, New York (1995). The labelling moiety will be visibly observable in conventional immunohistochemical detection techniques being, for example, a fluorescent dye such as fluorescein, a radioisotope, a colloidal label, such as colloidal gold or colored latex beads, an enzyme label, or any other known labelling complex. Such stains may be prepared by conventional techniques, for example as described in Manson, *Immunochemical Protocols: Methods in Molecular Biology Vol.* 10, Humana Press, Totowa, N.J. (1992), Beesley, *Immunocytochemistry: A Practical Approach*, IRL Press, Oxford, England (1993), the disclosure of which is herein incorporated by reference.

In the above described embodiments, methods have been explained for examining the effects of ethanol and therapeutic agents which affect these either in vivo or in vitro, and it will be readily apparent to one skilled in the art that these techniques may be applied to a number of problems. Determination of the localization of the Cα-subunit of PKA, δPKC, εPKC or any other ethanol indicative protein under investigation described above has been carried out manually, by visual observation. This procedure may be automated, for example by computer-based image recognition, or assays may be developed in which the localization of the protein is determined without visualization, for example by using reagents specific to the protein in combination with reagents having specific affinity for particular locations within the cell. Furthermore, the invention is not intended to be limited to the detection of the proteins mentioned above, but one skilled in the art may use other proteins whose behavior in the presence of ethanol is similar to those described above. Accordingly, the scope of the invention is not to be limited to the described embodiments, but is to be construed as incorporating all such variants which do not depart from the spirit thereof.

Another aspect of the invention is to provide methods for detecting the effects of ethanol on cells by measuring the phosphorylation of proteins that are differentially phosphorylated by, e.g., Cα in the presence and absence of ethanol. As previously discussed, exposure of cells to ethanol results in the translocation of Cα to the nucleus where the Cα catalytic subunit may phosphorylate (serine/threonine targets) a set of proteins that differs from the set of proteins available for phosphorylation in the cytoplasm, plasma membrane or Golgi. The identity of such proteins that are differentially phosphorylated in response to ethanol exposure may readily be determined using conventional assay techniques known to the person of ordinary skill in the art of molecular biology. For example, radioactively labeled phosphate may be added to cultured cells grown in both the presence and absence of ethanol. Proteins from the labeled cells may then be extracted and separated on a one or two dimensional gel system. Isolated phosphorylated proteins may then be visualized by autoradiography and related techniques. After separation and visualization, changes in the level of phosphorylation of different proteins may be determined by comparing the results obtained from cells exposed to ethanol with the results obtained from cells not exposed to ethanol. For example, proteins that are differentially phosphorylated by Cα in response to ethanol may be identified, e.g., by amino terminus amino acid residue sequencing. Proteins that are differentially phosphorylated by Cα in response to cellular ethanol exposure may be used in assays for the exposure of cells to ethanol. Furthermore, these differentially phosphorylated proteins may be used as the targets when screening for compounds that modulate the cellular effects of ethanol. Such assays include assays involving the steps of measuring the phosphorylation of differentially phosphorylated proteins. Compounds could be screened by measuring their effects on phosphorylation of these differentially phosphorylated proteins.

Cells for use in the subject screening assays for compounds that modulate the effects of ethanol may be primary cells derived directly from a subject or may be cells from a cell line. Such assays include assays in which Cα, δPKC or εPKC cellular localization is measured and assays in which the quantity of RI, αPKC, δPKC, or εPKC is measured. Preferably, the cells used in the assay are from cell line cells, more preferably the cells are from a neuroblastoma cell line. Cell line cells are preferred for use in the subject screening assays because they provide consistency between assays. Cells for use in the assays of the invention may be obtained from cells cultured in vitro and include cells derived from brain or neural tissue, particularly NG108-15 neuroblastoma X glioma cells.

Another aspect of the invention is to provide kits for carrying out the subject methods. Kits generally contain one or more reagents necessary or useful for practicing the methods of the invention. Reagents may be supplied in pre-measured units so as to provide for uniformity and precision in test results. Kits for determining the exposure of cells to ethanol by means of determining the intracellular localization of Cα, δPKC or εPKC comprise a stain specific for Cα, δPKC or εPKC. Such kits may further comprise one or more of the following items: additional reagents required for the detection of Cα, δPKC or εPKC that has complexed with the stain, positive controls, negative controls, equipment for obtaining tissue samples, and the like. The invention also provides kits for determining the exposure of cells to ethanol by means of measuring the amount of RI, αPKC, δPKC, or εPKC. These RI, αPKC, δPKC, or εPKC measurement kits comprise a stain specific for RI, αPKC, δPKC, or εPKC. The RI, αPKC, δPKC, or εPKC measurement kits may further comprise one or more of the following items: additional reagents for the detection of RI, αPKC, δPKC, or εPKC complexed with the stain; positive controls for RI, αPKC, δPKC, or εPKC; negative controls for RI, αPKC, δPKC, or εPKC; RI, αPKC, δPKC, or εPKC solutions of known concentration; equipment for obtaining tissue samples, and the like. The invention also provides kits for testing compounds for their ability to modulate cellular responses to ethanol using the assay methods of the invention. Such kits are essentially the same as the kits described above for the measurement of Cα, δPKC or εPKC cellular localization and RI, αPKC, δPKC, or εPKC levels; however, such kits may further comprise a cell line useful for the detection of changes in Cα, δPKC or εPKC localization.

Exemplary experimental procedures for detecting localization of the Cα catalytic subunit of PKA, and the δ- and ε-subunit of PKC are described below, but these procedures are not critical, and other techniques will be apparent to those skilled in the art. These examples are offered by way of illustration and should not be construed as limitations of the invention.

EXAMPLES

A. Example 1
Ethanol Induced Translocation Of The Cα Catalytic Subunit Of PKA NG108-15 cells were plated onto single chamber slides in a defined medium at a density of approximately 40,000 cells/slide. The techniques and media used for growing the cells are not critical, and are known to those skilled in the art. Suitable techniques are described in Gordon et al., 1986, *Proc. Natl. Acad. Sci USA* 83:2105. The cells were maintained for an additional forty eight (48) hours in the defined media or the defined media containing various concentrations of ethanol (e.g. 25, 50, 100, 200 mM ethanol). The media were replaced by fresh media (with or without ethanol) daily and the slides were wrapped in parafilm to prevent ethanol evaporation. The cells were fixed with methanol on a cooled surface for two (2) to three (3) minutes, and the slides were then immersed twice for five (5) minutes each in phosphate buffered saline (PBS) on ice. After that, the cells were incubated with blocking buffer (1% normal goat serum in PBS containing 0. 1% Triton-X-100) at 4° C. for six (6) to twelve (12) hours and then incubated with primary antibody solution for forty eight (48) hours at 4° C. in a humidified chamber. The primary antibody solution was prepared from primary antibodies raised in response to Cα (available from Transduction Laboratories and other companies and Susan Taylor at University of California at San Diego) diluted in PBS containing 0.1% Triton X-100 and 2 mg/ml fatty acid free bovine serum albumin. The slides were washed as before and incubated in the appropriate FITC (fluoresceinisothiocyanate)-conjugated secondary antibody diluted in the same solution at 1:1000.

After twenty four (24) hours, the slides were washed and coverslipped using Vectashield™ mounting medium (Vector Labs) . The images in panels a and b of FIG. 1 were made using a BIORAD™ 1024 confocal microscope. The images in panels c and d of FIG. 1 were made using a Leica™ DMBR microscope equipped with a fluorescein filter.

To determine reversibility of exposure to ethanol, results shown in panel c of FIG. 1, represent cells that the cells were exposed to media containing 200 mM ethanol for forty eight (48) hours then washed three times with fresh media containing no ethanol and incubated without ethanol for an additional forty eight (48) hours. To determine specificity of binding of the stain, the results shown in panel d of FIG. 1, represent cells to which 0.1 mg/ml purified catalytic subunit was added to the primary antibody solution two (2) hours prior to incubation with the fixed cells.

Figure 2:
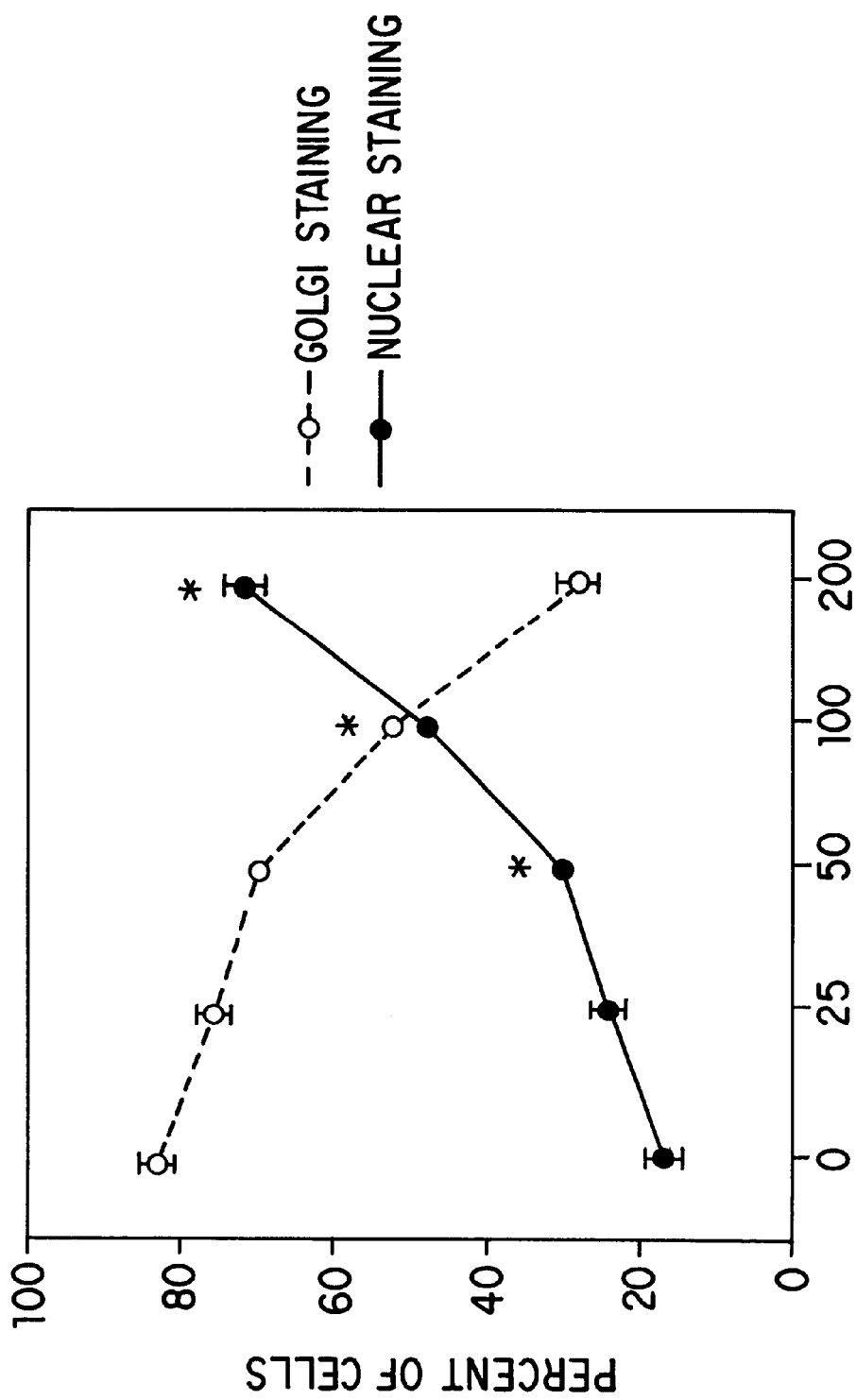
FIG. 2 is a graph showing the dependence of the percentage of cells exhibiting nuclear staining as compared to Golgi staining on the concentration of ethanol to which the cells have been exposed.
Figure 3A:
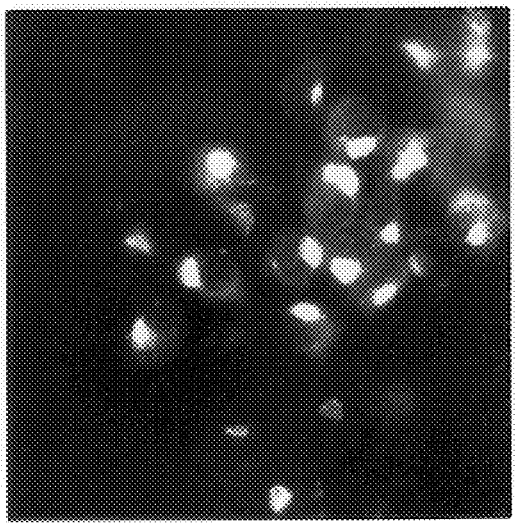
FIGS. 3A–D is a series of micrographs comparing the movement of the Cα subunit of PKA in cells exposed to ethanol against effects of treatment with various other agents as indicated.
Figure 3B:
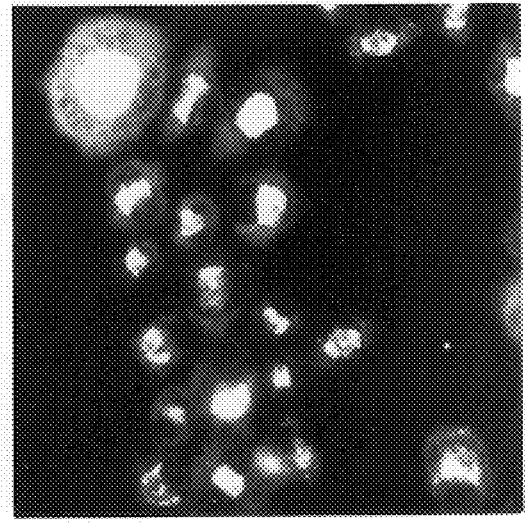
Figure 3C:
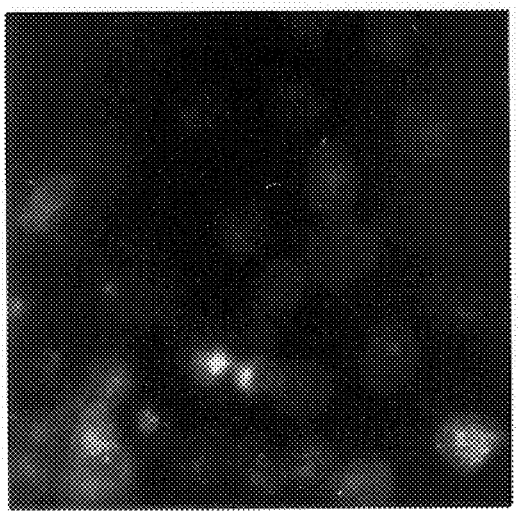
Figure 3D:
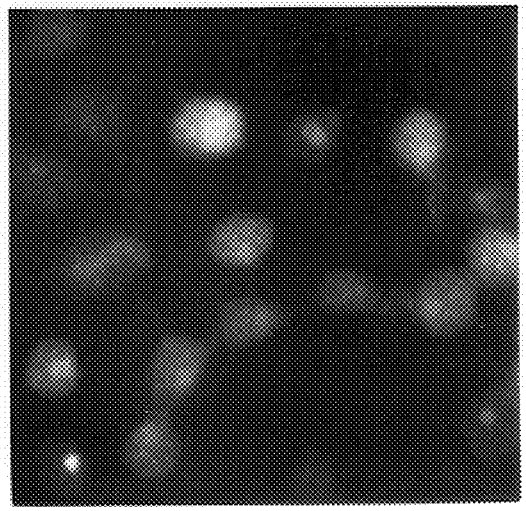

To obtain the numerical data shown in FIG. 2, random fields were selected on the slide and the cells within the field classified as either having primarily Golgi staining or primarily nuclear staining for Cα. Although using only two types of classification simplifies scoring of cells, it may be desirable to classify cells into a plurality of classification groups dependent on the degree of staining in each of several locations. In some instances, it may even be desirable to provide continuous variable classification of each cell, for example, if image intensity is measured at a given point in a cell. At least five (5) fields were classified for a total of at least one hundred (100) cells per slide. The observer was blind to the experimental condition of the slides. Data points are the mean +/−SEM (standard error of the mean copy) of four (4) experiments, *p<0.05.

The results obtained can be summarized as follows: NG108-15 cells, forming.a control, which had not been exposed to ethanol were stained with the specific stain. Cα was found in the perinuclear Golgi area in approximately 80% of the control cells, as depicted in panel a of FIG. 1. In the remaining 20% of the control cells, Cα was found predominately in the nucleus and cytoplasm. This localization of the Cα subunit to the Golgi has been previously observed by Nigg and co-workers. Nigg et al., 1985, *EMBO J.* 4:2801–2806. Cellular localization of Cα was further confirmed by co-localization with Golgi-specific markers, including mannosidase II, and ceramide. Nigg et al., supra.

Other cell samples were exposed to ethanol of varying concentrations (25, 50, 100, 200 mM), for a period of forty eight (48) hours, and the assay repeated. The results are shown in FIG. 2. As can be seen from FIG. 2, 75% of cells treated with 200 mM ethanol showed predominant localization of Cα in the nucleus. A micrograph of these cells is shown in panel b of FIG. 3. The results of these investigations serve as a reference to which a sample of cells suspected of being exposed to ethanol can be compared. To provide a screen for a drug or therapeutic agent to discover whether it has any effect on the cellular effects of ethanol, the above procedure can be repeated with the drug present in the growth medium in addition to alcohol. Since 100 mM ethanol is found to have a noticeable effect, and 200 mM ethanol is found to have a marked effect on the localization of Cα PKA, a screen for a drug can be provided employing a single growth medium preferably having an ethanol concentration of the order of at least 100 mM, and more preferably of 200 mM, or more. Of course, several growth media containing differing amounts of ethanol may be used, as described above, to investigate efficacy of the drug at varying levels of ethanol concentrations. This may be particularly useful for investigating the effects of a drug on long-term low-level exposure to ethanol.

The results from a control sample can be stored so that when screening for a particular drug, it is not necessary to conduct a control experiment each time. However, it is often desirable to conduct a control experiment whenever a drug is screened, to compensate for variations in other factors which may affect the results.

The above procedure is sufficient to form the basis for a screen. Additional factors having an effect on the localization of PKA Cα and activity of other PKA subunits have been identified. The following information may therefore be of assistance in assessing how the screening method may be affected by external factors.

Reversibility of the localization is demonstrated by panel c of FIG. 1 which is a micrograph of a similar sample forty eight (48) hours after withdrawal from the ethanol. As can be seen, the majority of the Cα had returned to the Golgi apparatus. In a screen for a drug, therefore, it is important to classify the cells relatively soon after removal from the medium, usually within forty eight (48), preferably within twelve (12) hours. Similarly, samples taken from patients should be classified soon after removal.

To test for specificity of the stain, the stain was preabsorbed by purified Cα prior to staining, and as can be seen from panel d of FIG. 1, virtually no staining resulted, indicating that the polyclonal antibody stain is specific to Cα.

The time dependence of the localization of the Cα and the effects of other substances were investigated (FIG. 3) as follows: NG108-15 cells were cultured as described above. After two (2) days in defined media, cells received media containing either 200 mM ethanol (panel b), 1 μM forskolin (panel d), or 10 μM PGE, (Prostaglandin E1) (panel c) for various lengths of time. Control cells received fresh media alone at the same time points. All slides were fixed four (4) days after plating and stained for Cα as described above. Similar experiments were performed using 25 mM and 50 mM ethanol over a period of four (4) to five (5) days; comparable results were obtained.

Figure 4:
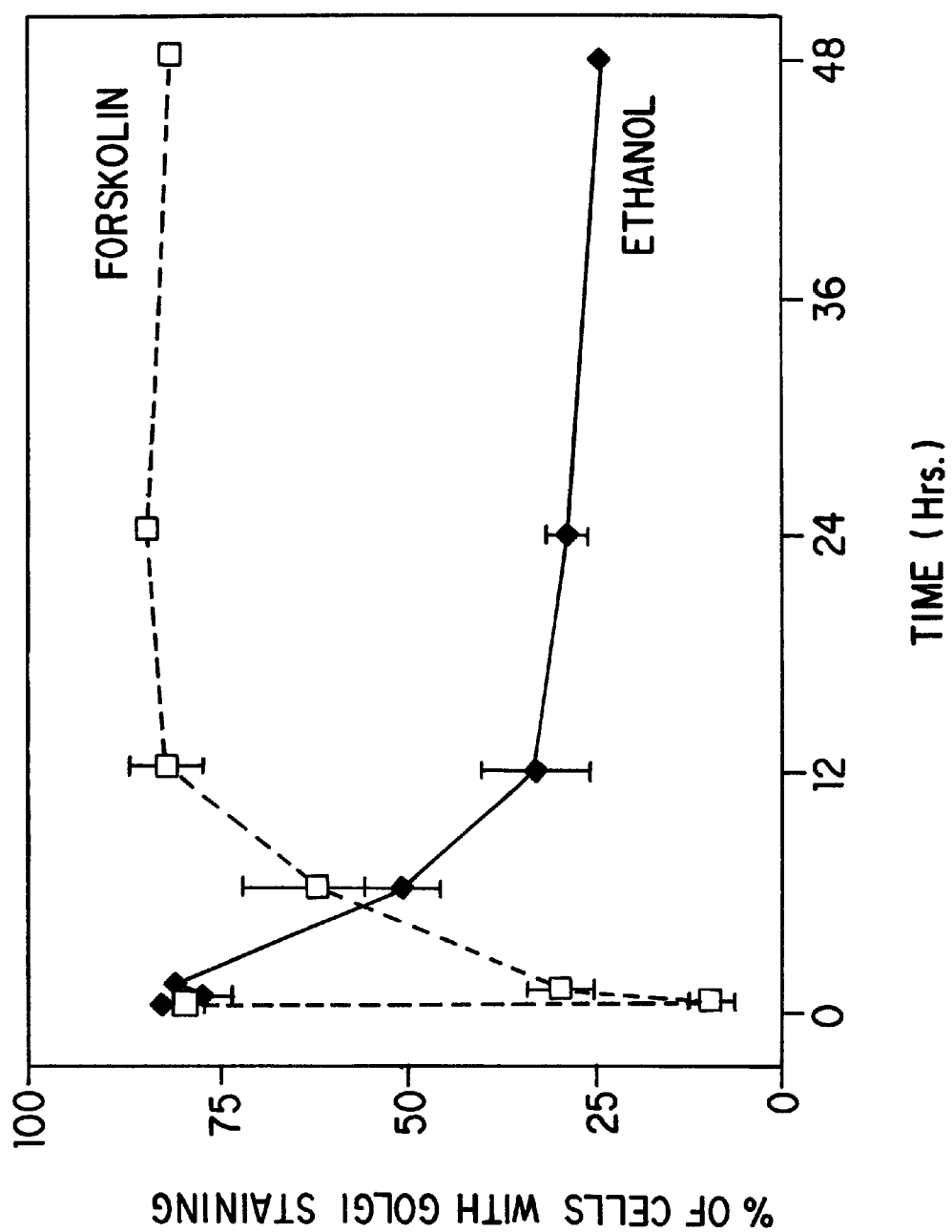
FIG. 4 shows the variation of the percentage of cells with Golgi staining over time, for cells exposed to ethanol, and for cells treated with forskolin.

To obtain the numerical results, depicted in FIG. 4, fields were selected as described above, and cells were scored as either having Cα staining confined primarily to the Golgi or extensive staining outside of the Golgi. Data points are the mean +/−SEM of three (3) experiments.

The results will now be discussed with reference to FIGS. 3 and 4. Panel a of FIG. 3 shows that the Cα was localized at the Golgi in the control cells, as before, and panel b of FIG. 3 shows that after forty eight (48) hours exposure to ethanol, Cα staining was found in the nucleus. This confirms the earlier described results.

Stimulation by 10 μm PGE, resulted in diffuse staining throughout the cell, as shown in panel c of FIG. 3. Similar results were achieved by treatment with 1 μM forskolin, as shown in panel d of FIG. 3. Maximal translocation of Cα away from the Golgi occurred after about thirty (30) minutes, with forskolin or PGE, which is when the micrographs shown in panels c and d of FIG. 3 were taken. This was followed by desensitization and a return of staining to the Golgi.

This is clearly contrasted with the effects of exposure to ethanol, where (see FIG. 4) after a relatively brief exposure to ethanol (from 30–60 minutes), little change in the localization of Cα was detected. After six (6) hours exposure to ethanol, translocation from the Golgi to the nucleus of the Cα was apparent, and after twelve (12) hours, most of the cells had developed prominent nuclear staining, with a corresponding decrease in Golgi staining. This staining remained through forty eight (48) hours of chronic exposure to ethanol.

Thus, in screening for the effect of drugs on ethanol uptake, best results will be obtained if the cells are left in the growth medium for at least about twelve (12) hours, and more preferably about forty eight (48) hours (two (2) days). The effects of ethanol exposure can be distinguished from the effects of other substances which produce a relatively temporary reversible change in Cα localization.

Figure 5A:
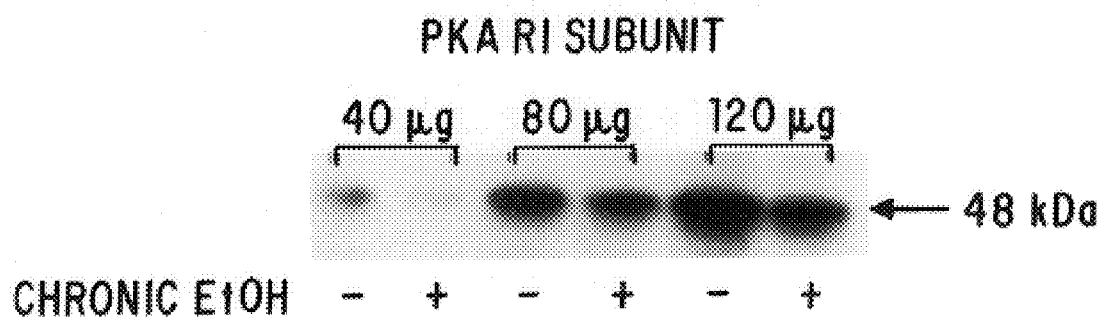
FIGS. 5A–B shows Western blot analysis of the Cα and RI PKA subunits in ethanol-exposed NG108-15 cells.
Figure 5B:
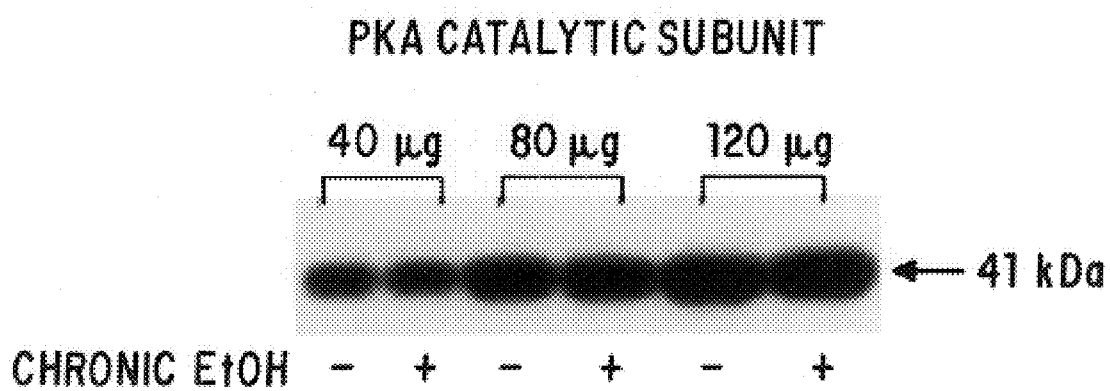

The investigation of movement and activity of other PKA subunits particularly type I (RI) and type II (RII) regulatory subunits was investigated. Stains using monoclonal antibodies, prepared by conventional immunocytochemistry techniques, analogous to those described above for the Cα subunit were used. No RII subunit was detected either by immunofluorescence or by Western blot analysis in NG108-15 cells, but the RI subunit was detected primarily on the Golgi apparatus. Ethanol was not found to have any significant effect on the localization of the RI subunit within the cell. It was, however, found that the amount of RI subunit was decreased by exposure to ethanol. Results of a Western blot analysis showing that exposure to 200 mM ethanol for forty eight (48) hours had no effect on the amount of Cα subunit, but produced a decrease of about 40% (43+/−3%) in the RI subunit are shown in FIG. 5. Thus, an alternative assay procedure can be provided by measuring the amount of PKA RI.

With the above results, the effects of ethanol on NG108-15 cells can thus be clearly identified. To produce a screen for therapeutic agents or drugs that modulate the cellular effects of exposure to ethanol, these cells can be exposed to ethanol in the presence of a drug whose activity is to be investigated, and the results compared to those obtained from cells exposed to ethanol in the absence of the drug.

B. Example 2

Ethanol Induced Translocation Of δPKC And εPKC

Figure 6A:
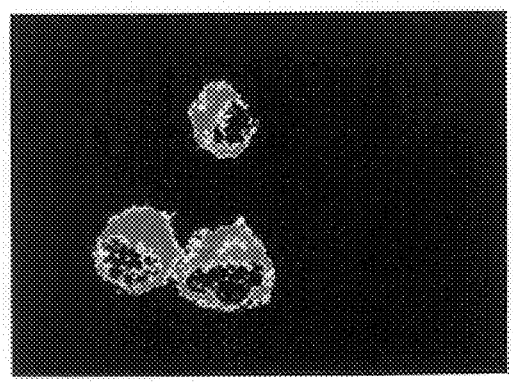
FIGS. 6A–C depicts immunohistochemical staining of δPKC in NG108-15 cells grown in defined medium in the presence or absence of EtOH or of PKC activation by PMA.
Figure 6B:
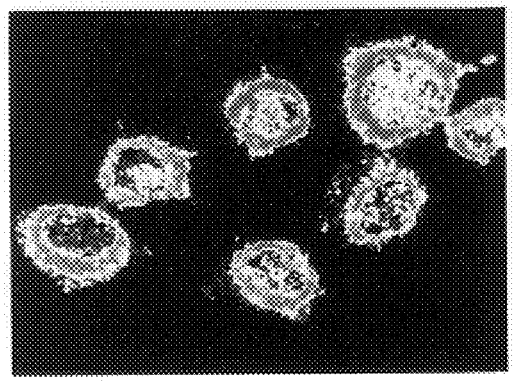
Figure 6C:
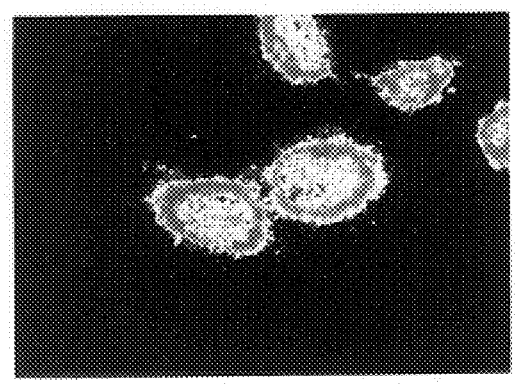
Figure 7A:
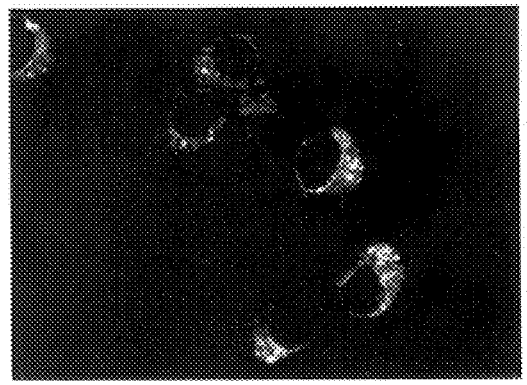
FIGS. 7A–C depicts immunohistochemical staining of δPKC in NG108-15 cells after a four (4) day exposure to 25 mM ethanol. The panels from top to bottom represent control, non-ethanol exposed cells; test cells exposed to 25 mM ethanol; and a control showing the specificity of the staining when the anti-ε antibody is preabsorbed with the immunizing peptide before labeling of the cells, respectively.
Figure 7B:
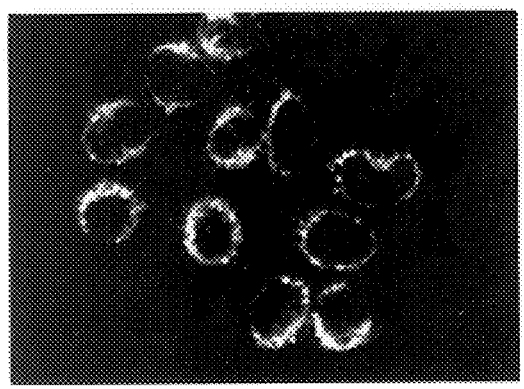
Figure 7C:
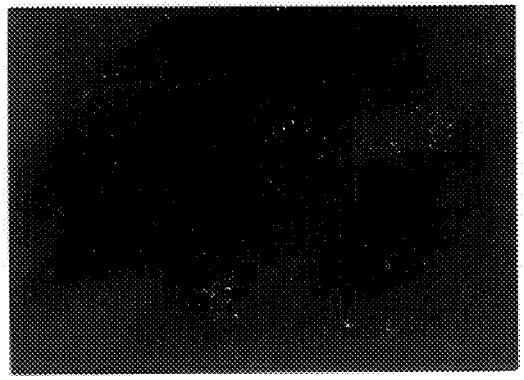

Immunohistochemistry of δPKC in NG108-15 cells, grown in defined medium, shows predominant Golgi staining (FIG. 6); approximately 70% of these cells show Golgi staining (TABLE I). After chronic ethanol exposure (48 hrs., 200 mM EtOH), δPKC is localized to the perinucleus and nucleus and absent from the Golgi (FIGS. 6 and 7). More that 90% of the cells show perinuclear and nuclear staining (TABLE I). The specificity of the fluorescence staining for δPKC is indicated by the absence of staining when the anti-δ antibody is preabsorbed with the immunizing peptide before labelling of the cells (FIG. 7). These results suggest that chronic ethanol exposure causes translocation of δPKC from the Golgi to the perinucleus and nucleus since there is little δPKC remaining in the Golgi area (TABLE I) after chronic ethanol exposure.

Figure 8A:
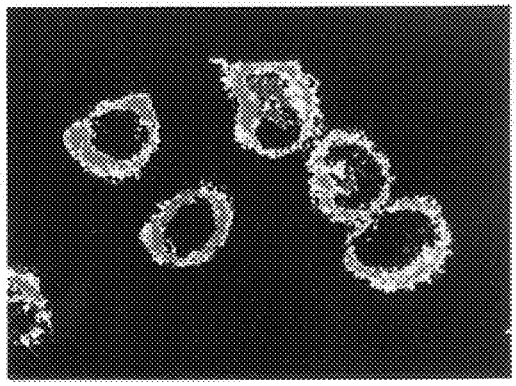
FIGS. 8A–C depicts immunohistochemical staining of εPKC in NG108-15 cells grown in defined medium in the presence or absence of EtOH or of PKC activation by PMA.
Figure 8B:
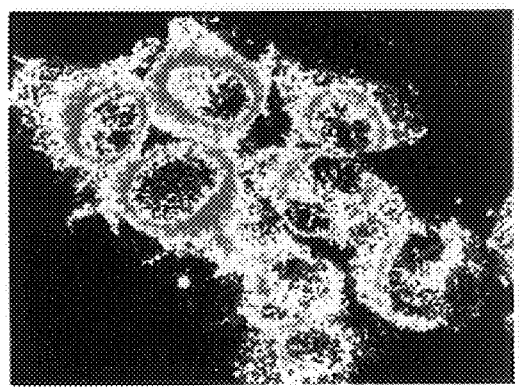
Figure 8C:
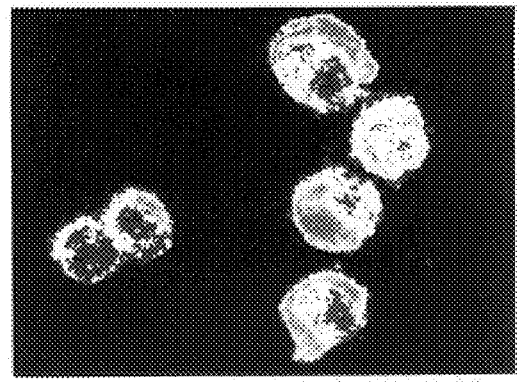
Figure 9A:
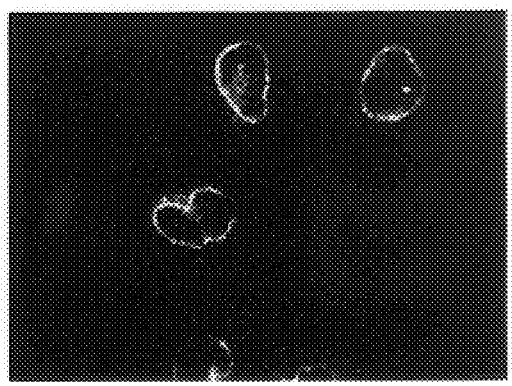
FIGS. 9A–C depicts immunohistochemical staining of εPKC in NG108-15 cells after four (4) day exposure to 25 mM ethanol. The panels from top to bottom represent control, non-ethanol exposed cells; test cells exposed to 25 mM ethanol; and a control showing the specificity of the staining when the anti-ε antibody is preabsorbed ("Pre.") with the immunizing peptide before labeling of the cells, respectively.
Figure 9B:
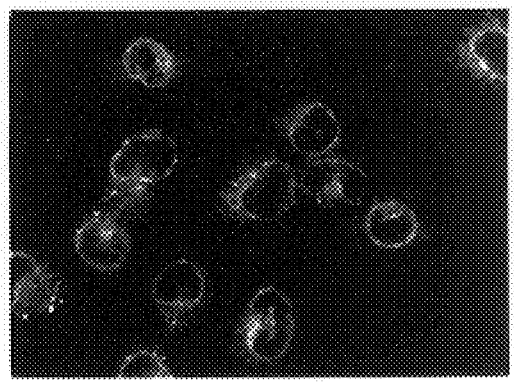
Figure 9C:
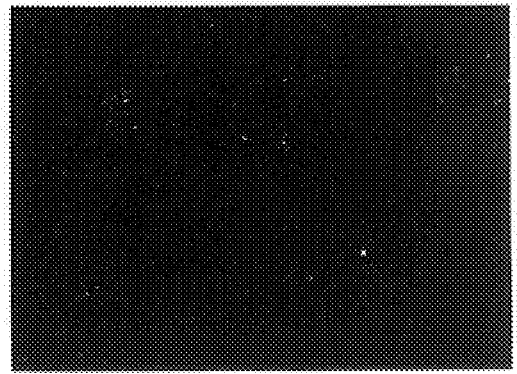

Ethanol also alters localization of εPKC. In naive cells, εPKC is localized to the perinucleus in more than 90% of the cells (FIGS. 8, 9 and TABLE I), with no measurable cytoplasmic staining. After chronic ethanol exposure, εPKC staining is observed throughout the cytoplasm in greater that 90% of the cells (FIGS. 8, 9 and TABLE I); perinuclear staining is still present in more that 90% of the cells (FIGS. 8, 9 and TABLE I). The staining for εPKC appears to be specific since no staining is observed when the anti-ε antibody is preabsorbed with immunizing peptide (FIG. 9). Ethanol-induced altered localization of δPKC and εPKC is also observed after exposure to 25 mM ethanol for four (4) days (FIGS. 7 and 9).

Ethanol-induced altered localization of PKC isozymes could be similar to that induced by phorbol esters or hormones or to sites different from these latter activators. Naive NG108-15 cells were, therefore, incubated in for ten (10) min. in 100 nM PMA, to then determine localization of δPKC and εPKC. On activation by PMA, the δ isozyme is mainly translocated to the perinucleus (FIG. 6), suggesting that ethanol-induced translocation of δPKC is to sites similar to those occupied after activation by PMA. In contrast, translocation of εPKC due to PMA activation results in nuclear and perinuclear cytoplasm localization of this isozyme, different from ethanol-induced translocation to the cytoplasm (FIG. 8).

The effects of ethanol on NG108-15 cells can thus be clearly identified by determination of the localization of δPKC and εPKC. To produce a screen for therapeutic agents or drugs that modulate the cellular effects of exposure to ethanol, these cells can be exposed to ethanol in the presence of a drug whose activity is to be investigated, and the results compared to those obtained from cells exposed to ethanol in the absence of the drug.

TABLE I

| δPKC | | | | εPKC | | | |
|---|---|---|---|---|---|---|---|
| Golgi Staining staining (%) cell | | Perinuclear staining (% cell) | | Perinuclear staining (% cell) | | Cytoplasms staining (% cell) | |
| Control | EtOH | Control | EtOH | Control | EtOH | Control | EtOH |
| 74 ± 7 (n = 5) | 2 ± 2 (n = 5) | 2 ± 2 (n = 5) | 93 ± 5 (n = 5) | 95 ± 2 (n = 5) | 94 ± 3 (n = 5) | 5 ± 2 (n = 5) | 94 ± 2 (n = 5) |

*The percentage of particular immunostaining was obtained from five (5) experiments, each experiment was counted in four (4) fields per slide, three (3) or four (4) different slides in the same experiment.

All patents, patents applications, and publications cited are incorporated herein by reference in their entirety.

The foregoing written specification is considered to be sufficient to enable one skilled in the art to practice the invention. Indeed, various modifications of the above described methods for carrying out the invention which are obvious to those skilled in the field of cellular biology or related fields are intended to be within the scope of the following claims.

What is claimed is:

1. A method for determining the exposure to ethanol of a sample comprising at least one mammalian test cell, comprising:
   (a) applying to said sample a stain having specific binding affinity for a subunit of PKA or an isozyme of PKC;
   (b) detecting said stain in the nucleus or perinucleus and/or Golei apparatus; and
   (c) detecting said exposure to ethanol by comparing a distribution of the stain with respect to said nucleus or perinucleus and the Golgi apparatus of said test cell compared to the distribution in a control cell of the same cell type which has not been exposed to ethanol and in which the stain is predominantly present in the Golgi apparatus, wherein predominant presence of the stain in the nucleus or perinucleus of said test cell is indicative of prior exposure of the sample to ethanol.

2. The method of claim 1, wherein the PKA subunit or PKC isozyme is PKA Cα or δPKC respectively.

3. The method of claim 1, wherein said sample comprises a plurality of test cells and said control cell is one of a plurality of control cells, wherein the stain being predominantly present in the nucleus or perinucleus in significantly more test cells than control cells is indicative of prior exposure of the sample to ethanol.

4. A method for determining the exposure to ethanol of a sample comprising at least one mammalian test cell, comprising:
   (a) applying to said sample a stain having specific binding affinity for δ-PKC;
   (b) detecting said stain in the perinucleus and nucleus and/or Golai apparatus of said test cell; and
   (c) detecting said exposure to ethanol by comparing the distribution of said stain in the perinucleus and nucleus and Golgi apparatus of said test cell compared to a control cell of the same cell type which has not been exposed to ethanol and in which the stain is predominantly present in the Golgi apparatus, wherein predominant presence of the stain in the perinucleus and nucleus of said test cell is indicative of prior exposure of the sample to ethanol.

5. The method of claim 4, wherein said stain comprises an antibody having a detectable moiety and a specific binding affinity for said δ-PKC.

6. The method of claim 5, wherein said detectable moiety comprises a fluorescein label conjugated to a second antibody.

7. A method for determining the exposure to ethanol of a sample comprising at least one mammalian test cell, comprising:
   (a) applying to said sample a stain having specific binding affinity ε-PKC;
   (b) detecting said stain in the cytoplasm and the perinucleus of said test cell; and
   (c) detecting said exposure to ethanol by comparing the distribution of said stain with respect to the cytoplasm and the perinucleus of said test cell with the distribution of said stain in a control cell of the same cell type which has not been exposed to ethanol and in which the stain is predominantly present in the perinucleus, wherein predominant presence of the stain in the cytoplasm of said test is indicative of prior exposure of the sample to ethanol.

8. A method for determining prior exposure to ethanol of a sample, comprising:
   (a) applying to said sample a stain having a specific binding affinity for a subunit of PKA or an isozyme of PKC, wherein said sample comprises at least one mammalian test cell;
   (b) comparing the amount of said stain in a first cellular subregion of said test cell with the amount of said stain in said first cellular subregion of a control cell of the same cell type which has not been exposed to ethanol; and
   (c) determining prior exposure of said sample to ethanol if said stain is present in said first cellular subregion of said test cell in a significantly greater amount than said stain is present in said first cellular subregion of said control cell, wherein
      (i) if said stain has specific binding affinity for PKA Cα, said first cellular subregion is the nucleus;
      (ii) if said stain has specific binding affinity for δPKC, said first cellular subregion is the nucleus or the perinucleus; and
      (iii) if said stain has specific binding affinity for εPKC, said first cellular subregion is the cytoplasm.

9. The method of claim 8, wherein said sample comprises a plurality of test cells and said control cell is one of a plurality of control cells, wherein the stain being predominantly present in the first cellular subregion in significantly more test cells than control cells is indicative of prior exposure of the sample to ethanol.

10. The method of claim 9, wherein the stain being predominantly present in the first cellular subregion in more than about 25% of the test cells is indicative of prior exposure of the sample to ethanol.

11. A method for determining the exposure of a mammalian subject to ethanol, comprising:
 (a) providing a sample containing at least one test cell from the subject;
 (b) staining said sample with a stain having specific binding affinity for a subunit of PKA or an isozyme of PKC;
 (c) comparing the amount of said stain in a first cellular subregion of said test cell with the amount of said stain in said first cellular subregion of a control cell of the same cell type which has not been exposed to ethanol; and
 (d) determining the exposure of said mammalian subject to ethanol if said stain is present in said first cellular subregion of said test cell in a significantly greater amount than said stain is present in said first cellular subregion of said control cell, and wherein
  (i) if said stain has specific binding affinity for PKA Cα, said first cellular subregion is the nucleus;
  (ii) if said stain has specific binding affinity for δPKC, said first cellular subregion is the nucleus or the perinucleus; and
  (iii) if said stain has specific binding affinity for εPKC, said first cellular subregion is the cytoplasm.

12. A screening method for determining whether a substance alters the effects of ethanol in at least one test cell, comprising:
 (a) providing a sample containing at least one mammalian test cell, wherein the test cell is a NG108-15 neuroblastoma X glioma cell;
 (b) providing a culture medium including ethanol;
 (c) including said substance in said culture medium;
 (d) exposing said test cell to said culture medium;
 (e) staining said test cell with a stain having specific binding affinity for a subunit of PKA or an isozyme of PKC, wherein the PKA subunit or PKC isozyme is PKA Cα or δ-PKC respectively;
 (f) detecting said stain in the nucleus or perinucleus and the Golgi apparatus;
 (g) classifying each test cell according to the distribution of said stain within the nucleus or perinucleus and the Golgi apparatus; and
 (h) determining whether said substance alters the effects of ethanol on said test cell by comparing the results of said classifying of said distribution of said stain in a control cell of the same cell type which has been exposed to ethanol but not to said substance and in which the stain is predominantly present in said nucleus or perinucleus, wherein predominant presence of said stain in the Golgi apparatus is indicative of alteration by said substance of the effects of ethanol in said test cell.

13. A screening method for determining whether a substance alters the effects of ethanol in at least one test cell, comprising:
 (a) providing a sample containing at least one mammalian test cell;
 (b) providing a culture medium including ethanol;
 (c) including said substance in said culture medium;
 (d) exposing said test cell to said culture medium;
 (e) staining said test cell with a stain having specific binding affinity for δ-PKC;
 (f) detecting said stain in the perinucleus and nucleus and Golgi apparatus of said test cell;
 (g) classifying each test cell according to the distribution of aid stain within the perinucleus and nucleus and Goldi apparatus; and
 (h) determining whether said substance alters the effects of ethanol on said test cell by comparing the results of said classifying of said distribution of said stain in a control cell of the same cell type which has been exposed to ethanol but not to said substance and in which the stain is predominantly present in the nucleus and perinucleus, wherein predominant presence of said stain in the Golgi apparatus is indicative of alteration by said substance of the effects of ethanol in said test cell.

14. The screening method of claim 13, wherein the test cell of step (d) is exposed to ethanol for at least twelve (12) hours.

15. The screening method of claim 13, wherein the test cell of step (d) is exposed to ethanol for about two (2) days.

16. A screening method for determining whether a substance alters the effects of ethanol in at least one test cell, comprising:
 (a) providing a sample containing at least one mammalian test cell;
 (b) providing a culture medium including ethanol;
 (c) including said substance in said culture medium;
 (d) exposing said test cell to said culture medium;
 (e) staining said test cell with a stain having specific binding affinity for a subunit of PKA or an isozyme of PKC, wherein the PKA subunit or PKC isozyme is PKA Cα or δ-PKC respectively;
 (f) detecting said stain in the nucleus or perinucleus and the Golgi apparatus;
 (g) classifying each test cell according to the distribution of said stain within the nucleus or perinucleus and the Golgi apparatus; and
 (h) determining whether said substance alters the effects of ethanol on said test cell by comparing the results of said classifying of said distribution of said stain in a control cell of the same cell type which has been exposed to ethanol but not to said substance and in which the stain is predominantly present in said nucleus or perinucleus, wherein predominant presence of said stain in the Golgi apparatus is indicative of alteration by said substance of the effects of ethanol in said test cell.

17. The screening method of claim 16, wherein the ethanol is provided at a concentration of at least 100 mM.

18. The screening method of claim 16, wherein the ethanol is provided at a concentration of at least 200 mM.

19. The method of claim 16, wherein said sample contains a plurality of test cells and said control cell is one of a plurality of control cells, wherein the stain being predominantly present in the Golgi apparatus in significantly more test cells than control cells is indicative of alteration by said substance of the effects of ethanol in said test cells.

20. The method of claim 19, wherein the stain being predominantly present in the Golgi apparatus in more than about 25% of the test cells is indicative of alteration by said substance of the effects of ethanol in said test cells.

21. A screening method for determining whether a substance alters the effects of ethanol in at least one test cell, comprising:
 (a) providing a sample containing at least one mammalian test cell;
 (b) providing a culture medium including ethanol;

(c) including said substance in said culture medium;

(d) exposing said test cell to said culture medium;

(e) staining said test cell with a stain having specific binding affinity for a subunit of PKA or an isozyme of PKC;

(f) comparing the amount of said stain in a first cellular subregion of said test cell with the amount of said stain in said first cellular subregion of a control cell of the same cell type which has been exposed to ethanol but not to the substance;

(g) determining said substance to have altered the effects of ethanol on said test cell if said stain is present in said first cellular subregion of said test cell in a significantly lesser amount than said stain is present in said first cellular subregion of said control cell, wherein
  (i) if said stain has specific binding affinity for PKA C$\alpha$, said first cellular subregion is the nucleus;
  (ii) if said stain has specific binding affinity for $\delta$-PKC, said first cellular subregion is the perinucleus or the nucleus; and
  (iii) if said stain has specific binding affinity for $\epsilon$-PKC, said first cellular subregion is the cytoplasm.

22. The method of claim 21, wherein said sample contains a plurality of test cells and said control cell is one of a plurality of control cells, wherein the stain being predominantly present in the first cellular subregion in significantly more test cells than control cells is indicative of alteration by said substance of the effects of ethanol in said test cells.

23. The method of claim 22, wherein the stain being predominantly present in the first cellular subregion in more than about 25% of the test cells is indicative of alteration by said substance of the effects of ethanol in said test cells.

24. A screening method for determining whether a substance alters the effects of ethanol in at least one test cell, comprising:

(a) providing a sample containing at least one mammalian test cell;

(b) providing a culture medium including ethanol;

(c) including said substance in said culture medium;

(d) exposing said test cell to said culture medium;

(e) staining said test cell with a stain having specific binding affinity for $\epsilon$-PKC;

(f) detecting said stain in the perinucleus and cytoplasm of said test cell;

(g) classifying each test cell according to the distribution of said stain within the perinucleus and cytoplasm; and (h) determining whether said substance alters the effects of ethanol on said test cell by comparing the results of said classifying of said distribution of said stain in a control cell of the same cell type which has been exposed to ethanol but not to said substance and in which the stain is predominantly present in the cytoplasm, wherein predominant presence of said stain in the perinucleus is indicative of alteration by said substance of the effects of ethanol in said test cell.

25. A screening method for determining whether a substance alters the effects of ethanol in at least one test cell, comprising:

(a) providing a sample containing at least one mammalian test cell;

(b) providing a culture medium including ethanol;

(c) including said substance in said culture medium;

(d) exposing said test cell to said culture medium;

(e) staining said test cell with a stain having specific binding affinity for PKA C$\alpha$;

(f) comparing the amount of said stain in the nucleus of said test cell with the amount of said stain in the nucleus of a control cell of the same cell type which has been exposed to ethanol but not to the substance;

(g) determining said substance to have altered the effects of ethanol on said test cell if said stain is present in the nucleus of said test cell in a significantly lesser amount than said stain is present in the nucleus of said control cell, and in said test cell said stain is now predominantly present in the Golgi apparatus.

\* \* \* \* \*